United States Patent
Brinson et al.

(10) Patent No.: US 6,433,205 B1
(45) Date of Patent: Aug. 13, 2002

(54) MAGNETIC SEPARATION FOR SILICON-CONTAINING MATERIALS

(75) Inventors: Jonathan Ashley Brinson, LaGrange, KY (US); John Eric Herman, Midland, MI (US); David William Snodgrass, Madison, IN (US); Hidehiko Hosokawa, Ichihara (JP)

(73) Assignees: Dow Corning Corporation, Midland, MI (US); Dow Corning Toray Silicone Company, Limited, Tokyo (JP)

( * ) Notice: Subject to any disclaimer, the term of this patent is extended or adjusted under 35 U.S.C. 154(b) by 0 days.

(21) Appl. No.: 10/050,617

(22) Filed: Jan. 15, 2002

(51) Int. Cl.$^7$ .................................................. C07R 7/16
(52) U.S. Cl. .................. 556/472; 252/183.13; 556/466; 209/214
(58) Field of Search ........................ 209/214; 556/472, 556/466; 252/183.13

(56) References Cited

U.S. PATENT DOCUMENTS

| | | |
|---|---|---|
| 2,380,995 A | 8/1945 | Rochow |
| 2,389,931 A | 11/1945 | Reed et al. |
| 3,133,109 A | 5/1964 | Dotson |
| 3,860,514 A * | 1/1975 | Lee et al. ................ 209/214 X |
| 4,054,513 A * | 10/1977 | Windle ........................ 209/214 |
| 4,218,310 A * | 8/1980 | Morey ........................ 209/214 |
| 4,281,149 A | 7/1981 | Shade |
| 4,307,242 A | 12/1981 | Shah |
| 4,810,368 A * | 3/1989 | Seider et al. ........... 209/214 X |
| 5,147,527 A | 9/1992 | Hettinger |
| 5,334,738 A | 8/1994 | Pachaly et al. |
| 5,349,921 A | 9/1994 | Barraclough et al. |
| 6,194,337 B1 | 2/2001 | Goolsby et al. |
| 6,264,843 B1 | 7/2001 | Weisner |

OTHER PUBLICATIONS

M.G.R.T. de Cooker, et al., "The Influence of Oxygen on the Direct Synthesis of Methylchlorosilanes", Jour. Organmetallic Chem. 84, 1975pp305–316.

Svoboda, Ja., "Magnetic Methods for the Treatment of Minerals", Developments in Mineral Processing–8, ISBNO–44–42811–9, Elsevier, NY 1987.

"Magnetic Separation", Kirk–Othmer Encyc. of Chemical Technology, 3rd Ed., 1978m John Wiley & Sons, NY vol. 15, pp708–732.

Wang, et al., Magnetic and Electrical Separation, Purification of Fine Powders by a Superconducting HGMS with Vibration Assistance, vol. 10(2000).

U. Birkholz, et al., Physica Status Solidi, 1969, No. 34, pp. K181–K184.

D. Mandrus, et al., Physical Review B, vol. 51, No. 8, Feb. 1995,pp.4763–4767.

O. Kubaschewski, Iron–Binary Phase Diagrams, Springer–Verlag, 1982, pp. 136–139.

Margaria, T., Anglezio, J.C., Servant, C., Intermetallic Compounds in Metallurgical Silicon, INFACON 6, Proceedings of the 6th International Ferroalloys Congress, Cape Town, vol. 1, Johannesburg, SAIMM, 1992, pp 209–214.

Maxwell, E., "Mutual Inductance Bridge for AC Susceptibility Measurements at Low Frequencies", Review of Scientific Instruments, vol. 36, 1965, pp553–554.

* cited by examiner

*Primary Examiner*—Paul F. Shaver
(74) *Attorney, Agent, or Firm*—Robert L. McKellar (57) ABSTRACT

Magnetic separators are used for treating silicon-containing materials from chlorosilane reactors to remove magnetically influenced components in the silicon-containing materials. The removal of such impurities allows for enhanced reactivity of the silicon-containing materials in processes wherein the silicon-containing materials are raw materials for the production of silicon based compounds, such as, for example, basic alkylhalosilanes such as dimethyldichlorosilane, methyldichlorosilane, and other chlorosilanes such as trichlorosilane, which chlorosilanes are useful in the preparation of valuable silicon-containing products.

32 Claims, 2 Drawing Sheets

MAGNETIC SEPARATION FOR SILICON-CONTAINING MATERIALS

The invention disclosed and claimed herein deals primarily with the use of magnetic separators for treating silicon-containing materials from a fluid bed reactor to remove magnetically influenced components in the silicon-containing materials. The removal of such components allows for enhanced reactivity of the silicon-containing materials in processes wherein the silicon-containing materials are raw materials for the production of silicon based compounds, such as, for example, basic alkylhalosilanes such as dimethyldichlorosilane, methylhydrogendichlorosilane, and other chlorosilanes such as trichlorosilane, which chlorosilanes are useful in the preparation of valuable silicon-containing products.

BACKGROUND OF THE INVENTION AND PRIOR ART

As indicated Supra, certain valuable halosilanes, that is, the halosilanes that form essentially the basis for the entire silicone products industry, are produced from the reaction between elemental silicon and an alkylhalide at elevated temperatures in the presence of a copper-based catalyst and various promoters. Other similar reactions are carried out to produce other silanes, for example, the preparation of trichlorosilane, which is a basic building block for the production of silicon metal.

There are literally hundreds of patents and publications directed to the basic reaction to produce the alkylhalosilanes, known in the industry as the Direct Process, the most fundamental and earliest being U.S. Pat. No. 2,380,995, that issued August 1945 to Rochow, directed to the chemical process and U.S. Pat. No. 2,389,931, that issued in November, 1945 to Reed, et al., directed to the fluidized bed reactors in the Direct Process.

The main purpose of the Direct Process is to make dimethyldichlorosilane, however, other silanes are produced such as methyltrichlorosilane, trimethylchlorosilane, tetramethylsilane and methyldichlorosilane, and other chlorosilanes and various methylchlorodisilanes, which find limited commercial use, along with direct process residue which is a combination of numerous compounds which are present in minor amounts and are not essentially commercially useful wherein the residues are high boiling having normal boiling points greater than about 71° C. These residual materials are well described in the literature.

There is a constant effort in the industry to enhance the Direct Process so that it is more selective in terms of producing the main component, dimethyldichlorosilane, and is more efficient to provide higher yields at a faster rate. In addition, intimate control of the process is desired such that when compounds other than dimethyldichlorosilane are desired, such as methyldichlorosilane, the process can be controlled to generate these compounds in higher yields.

Unfortunately, the commercial process as currently operated results in less control of the reaction as it proceeds, and this is thought to be due to the accumulation of impurities in the fluid bed reactors as the reaction within the fluid bed reactors progresses. In fact, the process is initially very active and highly selective to products of interest. Over time, performance degrades, allegedly due to the impurity buildup, and thus, the process has to be shut down periodically and the fluid bed contents purged, regenerated or refurbished in order to return the process to an acceptable yield level and rate of reaction, and more importantly, the selective formation of dimethyldichlorosilane. Metallurgical grade silicon typically contains 0.4% weight Fe, 0.15% weight Al, 0.08% weight Ca and 0.03% weight Ti (see U.S. Pat. No. 5,334,738 to Pachaly). The non-silicon metals form a range of intermetallic species such as $FeSi_2$, $CaSi_2$, $FeSi_2Ti$, $Al_2CaSi_2$, $Al_8Fe_5Si_7$, $Al_3FeSi_2$, $Al_6CaFe_4Si_8$, $FeSi_{2.4}Al$, and the like, which are also described in the open literature.

The selectivity of the formation of the chlorosilanes has been defined by Dotson, in U.S. Pat. No. 3,133,109, that issued May 12, 1964, as the ratio of organotrichlorosilane (T) to diorganodichlorosilane (D) (the T/D ratio), and it is generally desired to have this ratio below about 0.35 The modern objective is to minimize this ratio. Whenever used herein, the term "desired ratio" means the desired T/D ratio.

A further publication regarding the various factors affecting the degree of usage of the silicon in the Direct Process can be found in M. G. R. T. de Cooker, et. al., "The Influence of Oxygen on the Direct Synthesis of Methylchlorosilanes", Journal of Organometallic Chemistry, 84, (1975), pp. 305 to 316, in which de Cooker discloses that during the Direct Process synthesis, a gradual deactivation of the contact mixture surface occurs. He speculates that this deactivation may be caused by a number of factors. For example, the deposition of carbon and carbonaceous products may block part of the surface. Furthermore, the activity can be decreased by decreasing the content of the promoters on the contact mixture surface per se, for example, as caused by the evaporation of $ZnCl_2$, by the accumulation in the reactor of elements present as contaminants in the silicon, for example, iron, by the increase of free copper on the surface causing enhanced cracking, or by the blocking of the reactive sites by reaction of the contact mixture with traces of oxygen, yielding silicon and copper oxides. Silicon used in the experiments as disclosed in that article was technical silicon, as opposed to metallurgical silicon, wherein the main impurities of the technical silicon were described as being 0.4% weight Fe, 0.1% weight Al and 0.3% weight of each of Ca and Mg, and before use, the silicon was washed with water, dried, and treated with a magnet to remove part of the iron present in the silicon.

Thus, there is a need to overcome the impurity buildup and allow the reaction to run longer, with greater efficiency and increased yields, with better control over the products that are produced. Several references discuss impurities and their removal by withdrawing a stream from the reactor, separating an impurities-lean portion and returning it to the reactor. The term "content ratio" as used herein is calculated as the ratio of the weight percent of a given element in an impurities-rich fraction divided by the weight percent in an impurities-lean fraction. A content ratio of 1.0 indicates that there are equal concentrations of the given element in rich and lean fractions and thus no separation occurred for that element.

One solution for the removal of the impurities from the fluid bed reactants during the course of the reaction and thus decrease the impurity buildup in the reactors is disclosed in U.S. Pat. No. 4,307,242 that issued to Shah et al. on Dec. 22, 1981 in which a size classification method, e.g., aerodynamic centrifugal classifier, is used.

U.S. Pat. No. 4,281,149, that issued Jul. 28, 1981 to Shade describes a means of abrading a portion of the silicon particles in the reactor so surface poisoning is overcome and fresh reaction surfaces are exposed. Whenever used herein, the term "abraded" or "abrasion" means the processes set forth in Shade, which disclosure is incorporated herein by reference for what it teaches about the abrasion of solid particles from reactors.

The inventors herein are aware of other disclosures in the prior art that deal with the separation of metals from divided solid materials using magnetic separation technologies. There are two such disclosures from the refinery industry, neither of which deal with the magnetic separation of components from silicon-containing materials. One such piece of prior art is U.S. Pat. No. 5,147,527, that issued Sep. 15, 1992 to Hettinger, which discloses the magnetic separation of high metals-containing catalysts into low, intermediate and high metals, and active catalyst. Thus, the patent describes an improved process for converting carbo-metallic oils into lighter products using catalysts, the enhancement being a process of passing a portion of the catalyst particulates through a high strength magnetic field of at least one kilogauss and field gradients of at least 10 kilogauss/inch while conveying them on an electrostatic conducting belt and recycling the more active catalyst back to the process in which it was initially used.

A second disclosure can be found in U.S. Pat. No. 6,194,337, that issued on Feb. 27, 2001 to Goolsby, et al., in which the magnetic susceptibility of impure particles is enhanced to improve magnetic separation of undesirable contaminants in a catalyst.

Various references describe the application of magnetic forces to remove ferromagnetic and paramagnetic particulate impurities from mine ores and slurries. Svoboda, Jan., "Magnetic Methods for the Treatment of Minerals", *Developments in Mineral Processing-8*", ISBNO-44-42811-9, Elsevier, New York, 1987, reviews the state of magnetic separation technology. Other general references include "Magnetic Separation", *Perry's Chemical Engineers' Handbook*, McGraw-Hill, New York, $7^{th}$ Edition, 1998, pp. 19–49 and Oberteuffer, John, Wechsler, lonel, "Magnetic Separation", *Kirk-Othmer Encyclopedia of Chemical Technology*, $3^{rd}$ Edition, 1978, John Wiley & Sons, New York, Volume 15, pp.708–732. These references describe the technology of the induced magnetic roll separator, the permanent magnetic roll separator, the high gradient magnetic separator (HGMS), and open gradient magnetic separator, all of which are useful in the instant invention.

Some applications of magnetic separation have been demonstrated in silicon related chemistry. Wang, et al., in *Magnetic and Electrical Separation*, "Purification of Fine Powders by a Superconducting HGMS with Vibration Assistance, Vol. 10 (2000), pp. 161–178 demonstrate the ability of an HGMS to remove $Fe_2O_3$ from quartz. Seider, et al., in U.S. Pat. No. 4,810,368, that issued on Mar. 7, 1989 shows the beneficial separation of magnetic impurities from silicon carbide. Barraclough, et al., in U.S. Pat. No. 5,349,921, that issued Sep. 27, 1994, improved the impurity distribution in semiconductor grade silicon with the application of a 500 gauss magnetic field during crystal growth. Wiesner, in U.S. Pat. No. 6,264,843, that issued on Jul. 24, 2001, teaches how to remove impurities from the machining of semiconductor material wherein particles from saw blades or lapping plates can be magnetically separated from the cutting fluid used during the machining process for silicon.

Various authors have reported on magnetic susceptibility of silicon-containing materials. U. Birkholz, et al., report in Physica Status Solidi, 1969, No.34, pp. K181–K184 the magnetic susceptibility of $\alpha\text{-FeSi}_2$ in the temperature range of 0° C. to 1000° C. The $\alpha\text{-FeSi}_2$ has low magnetic susceptibility with a flat response in the temperature range of 0° C. to 400° C. Small amounts of excess silicon added make the magnetic susceptibility negative, that is, diamagnetic. D. Mandrus, et al., in Physical Review B, Vol. 51. No. 8, February 1995, pp. 4763–4767, report the magnetic susceptibility of FeSi in the temperature range of 50 K to 700 K. The FeSi shows a peak magnetic susceptibility at approximately 225° C. However, from the FeSi phase diagram from O. Kubaschewski, Iron- Binary Phase Diagrams, Springer-Verlag, 1982, pp. 136 to 139, and from reported intermetallic phases of commercial grade silicon, FeSi is not expected to be present in the feed silicon for the Direct Process.

None of the above-described references teach, show, or describe the magnetic separation of magnetic influenced species from silicon materials from fluid bed reactors to benefit the production of silanes. Also, none of the above-described references teach, show or describe an optimum temperature for magnetically separating the impurities expected to be present in the silicon.

The processes disclosed and claimed herein control impurity buildup in the fluid bed of the reactor and enhance the reaction therein to provide a more efficient process, better selectivity, better process control and longer run times for the reaction.

THE INVENTION

What is disclosed as the invention herein is the use of magnetic separators for treating silicon-containing materials from fluid bed reactors to remove magnetically influenced components in the silicon-containing materials, the essentially purified silicon-containing materials per se obtained thereby, the use of the purified silicon-containing materials in the production of alkylhalosilanes, the processes therefor, along with modifications of fluid bed reactants (silicon-containing materials) in conjunction with the magnetic separation of impurities therefrom, the purified silicon-containing materials that are obtained from comminuting treatments, modified in conjunction with the magnetic separator, the aerodynamic classification treatments, modified in conjunction with the magnetic separator, the materials that are obtained from abrading treatments in conjunction with the magnetic separator, and the combination of the comminuting-modification and aerodynamic classification-modification in conjunction with the magnetic separator application.

Thus, in addition, it is contemplated within the scope of this invention to combine the teachings of Shade to enhance the reactivity of the fluid bed reactants in conjunction with the magnetic separator aspect of the invention disclosed and claimed herein.

Further, it is contemplated within the scope of this invention to combine the teachings of Shah from the '242 patent to reduce the impurities of the fluid bed solids in conjunction with the magnetic separator aspect of the invention disclosed and claimed herein, and finally, it is contemplated within the scope of this invention to combine both the Shade and Shah teachings in combination and in conjunction with the magnetic separator aspect of this invention to obtain enhanced results in the use of fluid bed reactors to produce chlorosilanes.

And further, it is contemplated within the scope of this invention to combine the teachings of Shade from the '149 patent to reduce the impurities of the fluid bed solids in conjunction with the magnetic separator aspect of the invention disclosed and claimed herein.

As used herein, "magnetically influenced components" means those materials contained in the silicon-containing materials from a fluid bed reactor that are separable from the silicon-containing materials by the use of a magnetic field, and include, for example, those that are ferromagnetic, paramagnetic, or diamagnetic in nature, and including those materials that by their physical nature, or by their association with such ferro-, para-, or diamagnetic materials, are carried along with the ferro-, para-, or diamagnetic materials, and are thus capable of being removed from the fluid bed silicon-containing materials. Magnetically influenced components include those mixtures enriched in species preferentially attracted in the magnetic fraction and those depleted of species preferentially repulsed in the non-magnetic fraction. Magnetically influenced compounds might also include ferrimagnetic and antiferromagnetic species. Examples of the fluid bed silicon containing materials have been set forth Supra with regard to the discussion in the paragraph surrounding U.S. Pat. No. 5,334,738.

A first embodiment of this invention is a process of treating silicon-containing solid material used in a reactor for producing chlorosilanes, the process comprising subjecting the silicon-containing solid material that has been used in said reactor, to a magnetic separator apparatus to separate constituents in the silicon-containing solid material into a magnetic portion and a non-magnetic portion.

A second embodiment of this invention is a process where the silicon-containing solid material from the fluid bed of a fluid bed reactor is removed from the reactor wherein the process comprises removing the silicon-containing solid material from a fluid bed of a fluid bed reactor, subjecting the silicon-containing solid material to a magnetic separator apparatus to separate constituents in the silicon-containing solid material into a magnetic portion and a non-magnetic portion and then returning the non-magnetic portion of the silicon-containing solid material to a fluid bed of a fluid bed reactor. Note that this embodiment contemplates that the treated silicon-containing solid material may be returned to the reactor that it was removed from or may be returned and used in a different fluid bed reactor.

Another embodiment of this invention is the use of the above-described process in a process for the production of alkylhalosilanes and more specifically, in the Direct Process for the production of alkylhalosilanes and in a process for the production of trichlorosilane.

Yet another embodiment of this invention is the silicon-containing materials per se that are produced by subjecting them to magnetic separation in which the silicon-containing materials are reduced in impurities.

Still another embodiment of this invention is a process for the preparation of chlorosilanes wherein the process comprises providing a fluid bed reactor and charging the fluid bed reactor with comminuted silicon, at least one catalyst for a Direct Process reaction, and at least one promoter for the Direct Process reaction. Thereafter, providing an alkyl chloride to the fluid bed reactor to form a fluid bed in the reactor and allowing the comminuted silicon, catalyst, promoter, and alkyl chloride to interact and react to produce alkylchlorosilanes at a desired ratio and at a desired reaction rate. Thereafter, upon a certain increase in the desired ratio or a reduction in the desired rate of the reaction, subject the contents of the fluid bed to a process comprising treating the fluid bed contents by subjecting the fluid bed contents to a magnetic separator apparatus to separate constituents in the fluid bed contents into a magnetic portion and a non-magnetic portion. Thereafter, removing the magnetic portion of the fluid bed contents from the fluid bed of the fluid bed reactor and continuing the Direct Process.

A further embodiment is a process for the preparation of chlorosilanes. The process comprises providing a fluid bed reactor and charging the fluid bed reactor with comminuted silicon, at least one catalyst for a Direct Process reaction and, at least one promoter for the Direct Process reaction. Thereafter, providing an alkyl chloride to the fluid bed reactor to form a fluid bed in the reactor and allowing the comminuted silicon, catalyst, promoter, and alkyl chloride to interact and react to produce alkylchlorosilanes at a desired ratio and at a desired reaction rate. Thereafter, upon a certain increase in the desired ratio or a decrease in the desired reaction rate, subject the contents of the fluid bed to a process comprising treating the fluid bed contents by comminuting the fluid bed contents to abrade the solids or to reduce the average particle size of the solids therein and then subjecting the comminuted fluid bed contents to a magnetic separator apparatus to separate constituents in the fluid bed contents into a magnetic portion and a non-magnetic portion. The magnetic portion of the fluid bed contents are removed from the fluid bed of the fluid bed reactor and the Direct Process is continued.

Going to yet another embodiment of this invention, there is a process for the preparation of chlorosilanes, the process comprising providing a fluid bed reactor and charging the fluid bed reactor with comminuted silicon, at least one catalyst for a Direct Process reaction, and at least one promoter for the Direct Process reaction. Thereafter, providing an alkyl chloride to the fluid bed reactor to form a fluid bed in the reactor and allowing the comminuted silicon, catalyst, promoter, and alkyl chloride to interact and react to produce alkylchlorosilanes at a desired ratio and at a desired rate. Thereafter, upon a certain increase in the desired ratio or a decrease in the desired reaction rate, subject the contents of the fluid bed to a process comprising treating the fluid bed contents by reducing and removing impurities from the solids portion of the fluid bed contents by subjecting the fluid bed contents to a size classification method using an aerodynamic centrifugal classifier process and then subjecting the purified fluid bed contents to a magnetic separator apparatus to separate constituents in the fluid bed contents into a magnetic portion and a non-magnetic portion. Thereafter, removing the magnetic portion of the fluid bed contents from the fluid bed of the fluid bed reactor and continuing the Direct Process.

Still, there is provided another embodiment of this invention which is a process for the preparation of chlorosilanes, the process comprising providing a fluid bed reactor and charging the fluid bed reactor with comminuted silicon, at least one catalyst for a Direct Process reaction, and at least one promoter for the Direct Process reaction and thereafter, providing an alkyl chloride to the fluid bed reactor to form a fluid bed in the reactor. Thereafter, allowing the comminuted silicon, catalyst, promoter and alkyl chloride to interact and react to produce alkylchlorosilanes at a desired ratio and at a desired reaction rate and upon a certain increase in the desired ratio or a reduction in the desired reaction rate, subject the contents of the fluid bed to a process comprising treating the fluid bed contents by comminuting the fluid bed contents to abrade the solids or to reduce the average particle size of the solids therein and thereafter, reducing and removing impurities from the milled solids portion of the fluid bed contents by subjecting the fluid bed contents to a size classification method using an aerodynamic centrifugal classifier process. The purified fluid bed contents are then subjected to a magnetic separator apparatus to separate constituents in the fluid bed contents into a magnetic portion and a non-magnetic portion and thereafter removing the magnetic portion of the fluid bed contents from the fluid bed of the fluid bed reactor and continuing the Direct Process.

Going to yet another embodiment of this invention, there is a process for the preparation of chlorosilanes, the process comprising providing a fluid bed reactor and charging the fluid bed reactor with comminuted silicon, at least one catalyst for a Direct Process reaction, and at least one promoter for the Direct Process reaction. Thereafter, providing an alkyl chloride to the fluid bed reactor to form a fluid bed in the reactor and allowing the comminuted silicon, catalyst, promoter, and alkyl chloride to interact and react to produce alkylchlorosilanes at a desired ratio and at a desired rate, Thereafter, upon a certain increase in the desired ratio or a decrease in the desired reaction rate, subject the contents of the fluid bed to a process comprising treating the fluid bed contents by reducing and removing impurities from the solids portion of the fluid bed contents by treating the fluid bed contents by abrading the fluid bed contents to remove impurities form the surface of the fluid bed contents particles and thereafter subjecting the purified fluid bed contents to a magnetic separator apparatus to separate constituents in the fluid bed contents into a magnetic portion and a non-magnetic portion. Thereafter, removing the magnetic portion of the fluid bed contents from the process and continuing the Direct Process.

DETAILED DESCRIPTION OF THE INVENTION

As set forth Supra, there is disclosed herein a process for the use of magnetic separators for treating silicon-containing fluid bed materials to remove magnetically influenced components in the silicon-containing materials.

Figure 1:
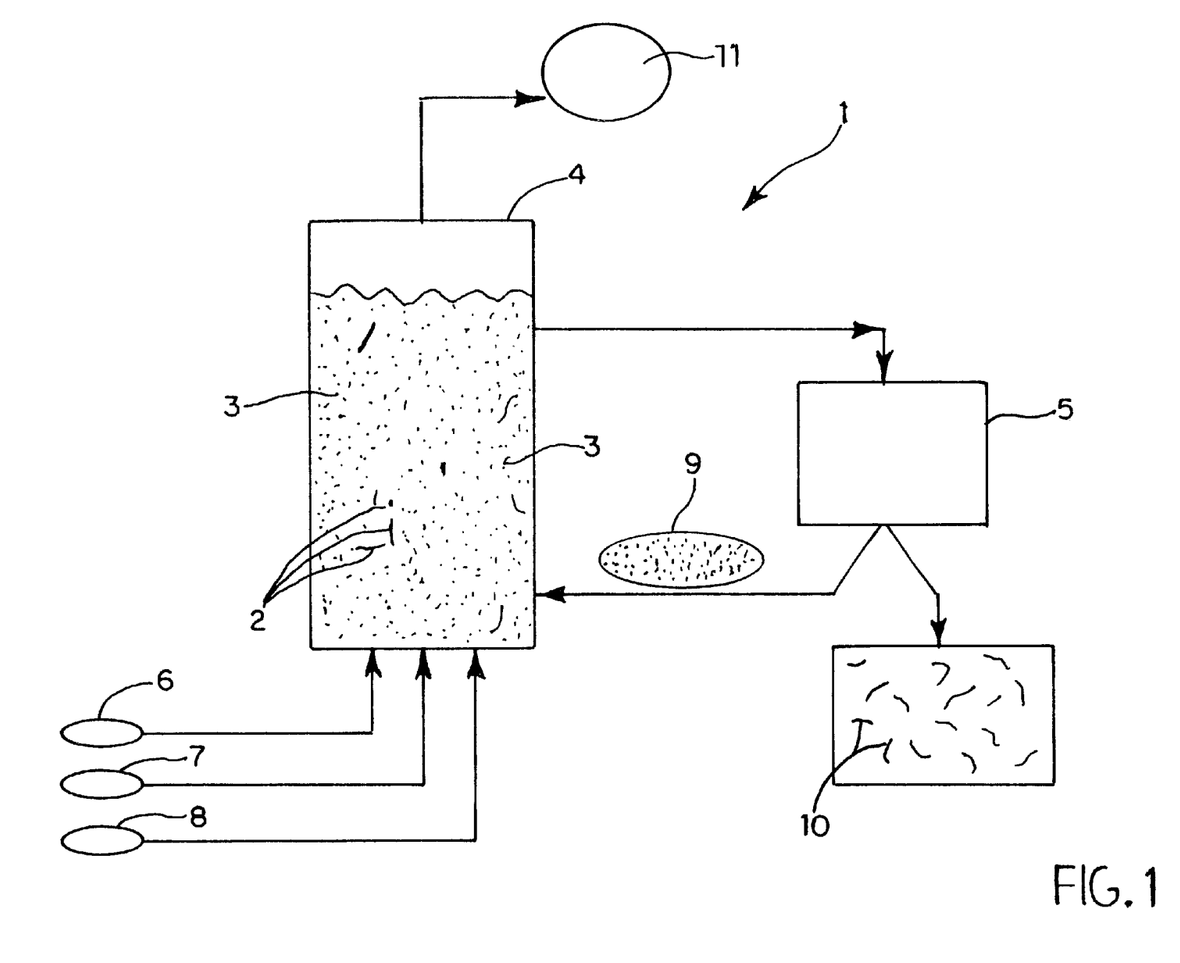
FIG. 1 is a schematic drawing of one embodiment of the process.

Turning to FIG. 1, there is shown therein a schematic diagram of the process and apparatus 1 for the magnetic separation of magnetically influenced components 2 in silicon-containing materials 3 wherein a portion of the reaction mass (silicon-containing solid materials 3) are removed from the fluidized bed reactor 4, subjected to the magnetic separator 5 and then returned to the fluidized bed reactor 4.

As shown by way of example, metallurgical grade silicon 6, methyl chloride 7, catalysts and promoters 8 are fed to a fluidized bed reactor 4. A magnetic separator 5 processes a portion of the reaction mass 3. The silicon-containing solid materials 3 may optionally be diverted from the fluidized bed reactor 3 to be processed by the magnetic separator 5, or alternatively, processed in-situ within the fluidized bed reactor 4 or treated by a process (not shown) to reduce the impurities before being moved to the magnetic separator 5. The silicon-containing solid materials 3 as the feed material can be removed continuously, intermittently, or according to a batch schedule. The non-magnetic fraction 9 can be returned to the original reactor 4 or a separate secondary reactor (not shown) for further reaction of the treated silicon-containing materials 3. The magnetic fraction 10 is removed from the original reactor 4 in order to control the impurities accumulation over time. The objective of this process is to improve the performance of the fluidized bed reactor and to improve the crude chlorosilane product 11 selectivity. The details of the actual use of the magnetic separator in this manner are set forth in the examples set forth infra.

As far as is known by the inventors herein, any magnetic separator devices that are effective for separating the magnetically influenced material are useful in the process of this invention. There are several commercial separators, some of which are described in Perry's Handbook and Kirk-Othmer Encyclopedia identified supra.

It should be understood by those skilled in the art that the metallurgical silicon that is used in reactors for the preparation of chlorosilanes can be treated with magnetic separators to remove magnetically influenced components prior to its use in such reactors, and it is contemplated within the scope of this invention to use such a treatment in conjunction with the processes disclosed and claimed herein, and especially when it is desired to remove "tramp" magnetically influenced components, especially iron, from such silicon. "Tramp" components are those components that are added to the metallurgical silicon through comminution processes that are applied to the silicon to reduce the size of the particles prior to its use in the reactors.

EXAMPLES

Example 1

A Carpco Model MIH(13) 111-5 high intensity induced roll magnetic separator manufactured by Outokumpu Technology Incorporated, Carpco Division, Jacksonville, Fla. was used to separate a sample of metallurgical grade silicon. The silicon was partially reacted with methyl chloride in a fluidized bed reactor before application in this example. The magnetic separator was set to process the sample at 180 rpm roll speed, 3 amp coil current, and 76% vibrator speed. The knife position was set at 87 degrees. The feed was separated into a magnetic fraction, a middle (intermediate) fraction, and a non-magnetic fraction. The elemental analysis is shown in Table 1 below. Iron shows a high content ratio of 14.65. Removal of iron and other non-silicon elements such as Al, Ca, Cr, etc. enhances the process and improves performance.

The relatively lower content ratio for copper is a desirable benefit. This indicates that separation of iron from an operating commercial fluidized bed reactor will remove relatively less of the copper catalyst present in the system. Copper (as elemental copper, a salt, or an oxide) is an expensive additive required to catalyze the reaction. Preferential removal of non-silicon, non-copper particles is a desirable feature of an impurities separation system.

Example 2

An Eriez model 50-4 dry vibrating magnetic filter (DVMF) was used to separate a sample of partially reacted silicon removed from a commercial fluidized bed reactor. The unit operated at 5000 gauss field strength. The cylinder was loaded with a ¼ inch expanded metal matrix that was vibrated vertically at 1200 rpm at an amplitude of 0.090 inches. The starting metallurgical grade silicon was comminuted in a ball mill and partially reacted with catalyst, promoters and methyl chloride. The feed to the DVMF was separated into a magnetic and non-magnetic fraction. The elemental analysis for this material is shown in Table 2 infra.

As shown in Table 2, the iron content ratio is high. The copper content ratio is relatively low. The carbon content ratio indicates that in addition to metallic impurities, carbonaceous deposits are also unexpectedly preferentially removed by magnetic separation. Other non-silicon, non-copper elements are also preferentially removed which enhances the process.

Example 3

The magnetic and non-magnetic fractions from Example 2 were analyzed using scanning electron microscopy (SEM) and energy dispersive spectroscopy (EDS). This analysis was performed to determine if magnetically susceptible metals were uniformly distributed within the silicon samples and if particles of certain known intermetallic impurities were more prevalent in the magnetic fraction when compared to the non-magnetic fraction. The samples were adhered to carbon tape on a graphite SEM stub. For this analysis, a thin layer of carbon was deposited onto the samples to make them conductive for the SEM/EDS analysis. Thirty particles in each sample were randomly chosen and analyzed to determine their atomic composition.

After the random analysis was completed, a "backscatter" analysis mode was employed. This mode showed particles with atomic weights higher than pure silicon. These areas were further explored to determine the composition of high atomic weight particles.

Most of the particles in the magnetic and non-magnetic fractions were highly pure silicon with greater than 90% weight silicon. In the magnetic fraction, thirteen of thirty particles contained greater than 0.1% weight iron. In the non-magnetic fraction, only one of thirty particles contained greater than 0.1% weight iron. In the randomly sampled magnetic fraction, two particles were observed with greater than 49% weight iron. With the machine in a backscatter mode, one further particle was identified with greater than 91% weight iron. No similar particles with greater than 30% weight iron were observed in the non-magnetic fraction. The elemental content of these high iron particles is consistent with the composition of grinding balls used in the ball mill used to comminute the lump silicon for use in this example. The grinder balls are gradually worn down, and the iron is thereby added to the powdered silicon. These three high iron particles are believed to be grinding ball fragments.

Several particles observed contained atomic compositions consistent with those previously reported in the open literature and attributed to intermetallic impurities commonly found in metallurgical grade silicon. For example, discrete particles of $Si_8Al_6Fe_4Ca$ can be observed in the magnetic fraction. In the random analysis of the magnetic fraction, two of the thirty particles are $Si_8Al_6Fe_4Ca$. A third $Si_8Al_6Fe_4Ca$ particle was located in the magnetic fraction when analyzed in the backscatter mode (non-random sampling). The atomic compositions of these particles are shown in Table 3 infra with a reference composition for the $Si_8Al_6Fe_4Ca$ phase from Margaria, T., Anglezio, J. C., Servant, C., "Intermetallic Compounds in Metallurgical Silicon, INFACON 6, *Proceedings of the 6th International Ferroalloys Congress*, Cape Town. Volume 1, Johannesburg, SAIMM, 1992, pp. 209 to 214. No $Si_8Al_6Fe_4Ca$ particles were found in the non-magnetic fraction.

Other non-silicon particles were observed with compositions substantially consistent with the reported compositions of the phases $FeSi_{2.4}Al$, $Si_2FeTi$, and $CaSi_2$ (with $CaCl_2$). The non-silicon metals particles observed were more prevalent in the magnetic fraction than in the non-magnetic fraction.

Example 4

The following demonstrates the benefit of partially reacting the silicon to improve magnetic separation. Metallurgical grade silicon was comminuted in a commercial ring roller mill and fed to a High Gradient Magnetic Separator (HGMS) capable of 20,000 gauss magnetic field. In this sample, the field strength was limited to 3000 gauss. The results can be found in Table 4, Infra.

There is virtually no concentration of non-silicon metals in this experiment. At the same field strength of 3000 gauss, a sample of silicon, partially reacted in a fluid bed reactor was processed. The results are presented in Table 5, infra.

Example 5

To demonstrate the harmful effect of iron on the direct process, iron powder was intentionally added to a sample of silicon and reacted in a laboratory direct process reactor. Numerous reactions with commercial metallurgical grade silicon were made to establish that the reactor system was in a state of statistical process control. A standard copper based catalyst and promoters were added to a batch of silicon and reacted with methyl chloride for 44 hours in a temperature-controlled oven at 320° C. To the test samples, iron powder was added to double the iron content. The iron used was Alpha Products catalog number 00170, 325 mesh (44 micron), 99.9+% purity on a metals basis. The results are shown on Table 6 infra. As shown from the Table, the elemental iron significantly harmed the T/D ratio.

Example 6

Figure 2:
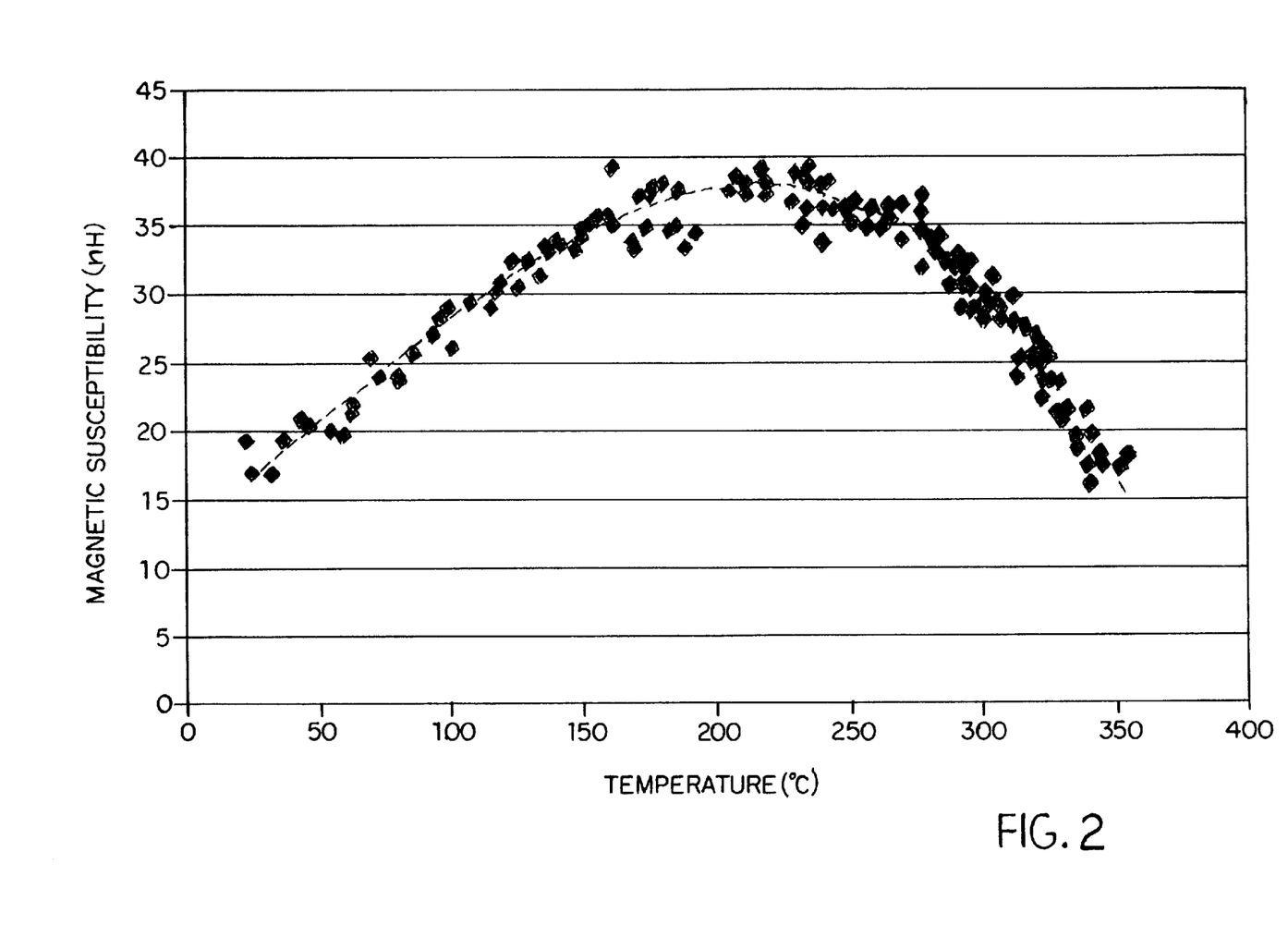
FIG. 2 is a graph of the results of the experiment set forth in Example 7.

A portion of the magnetic fraction from Example 2 was tested to demonstrate the effect of temperature on the magnetic susceptibility of the material. The powdered silicon was placed in a 3 mm diameter quartz tube. The tube was evacuated and sealed with a torch. The magnetic susceptibility was tested with a Hartshorn mutual inductance bridge constructed according to the description by Maxwell, E., "Mutual Inductance Bridge for AC Susceptibility Measurements at Low Frequencies", *Review of Scientific Instruments*, Volume 36, 1965, pp. 553–554. The test coils consisted of a primary coil with a winding density of 3150 turns/meter and two secondary coils wound in opposition with 120 turns each. The mutual inductance between one of the secondary coils and the primary coil was measured. Measurements were made of the empty coils and the sample of the magnetic fraction from Example 2. The measurements were calibrated, and the empty coil data was subtracted from the sample measurements and then normalized to units of nanohenries. A graph of results is shown in FIG. 2 with a drawn curve of best fit. As can be observed from FIG. 2, a peak magnetic susceptibility was observed at approximately 217° C.

Comparative Example 1

The various separation methods are compared to show the utility of the preferred magnetic processes compared to other magnetic and prior art non-magnetic separation methods. For comparison to a non-magnetic separation method, size classification, for example, separation of cyclone fines, as described by Shah et al. in U.S. Pat. No. 4,307,242 is included. The feed material is separated into two fractions. Fraction 1 is the iron-rich fraction that is the magnetic fraction of the examples in this invention or the fine fraction of the Shah examples. Fraction 2 is the purified fraction that is the non-magnetic fraction of the examples in this invention or the coarse fractions in the Shah examples. Example numbers for the Shah patent refer to those descriptions designated in the patent. The magnetic fraction designations are identified above. The comparison is set forth in Table 7, infra.

TABLE 1

Magnetic Separation With an Induced Roll Magnet

| | Total Weight in grams | Weight Fraction % | Al wt. % | Ca wt. % | Cu wt. % | Fe wt. % |
|---|---|---|---|---|---|---|
| Feed | 207.48 | 100% | 0.202 | 0.106 | 4.3 | 1.04 |
| Magnetic fraction | 21.00 | 10.4 | 0.811 | 0.23 | 5.73 | 6.11 |
| Middle fraction | 71.53 | 35.5 | 0.119 | 0.079 | 4.51 | 0.38 |
| Non-magnetic fraction | 108.96 | 54.1 | 0.130 | 0.081 | 3.46 | 0.417 |
| Content ratio | | | 6.24 | 2.84 | 1.66 | 14.65 |

Note:
Additional metals were concentrated in the magnetic fraction. These include Cr, K, Mg, Mn, Na, Ni, P, Sn, Ti, V and Zn that had content ratios from 1.30 to 15.36.

TABLE 2

Magnetic Separation with a DVMF

| | Total Weight Grams | Weight Fraction % | Al wt. % | C wt. % | Ca wt. % | Cu wt. % | Fe wt. % |
|---|---|---|---|---|---|---|---|
| Feed | 4641.6 | 100% | 0.24 | 0.34 | 0.15 | 4.6 | 1.0 |
| Magnetic fraction | 132.6 | 2.9 | 2.40 | 1.40 | 0.85 | 6.1 | 15.0 |
| Non-magnetic fraction | 4509.0 | 97.1 | 0.17 | 0.32 | 0.15 | 4.6 | 0.58 |
| Content ratio | | | 14.20 | 4.38 | 5.67 | 1.33 | 25.86 |

Note:
Additional elements including Mg, Mn, P, Sn, Ti, and Zn had content ratios from 1.84 to 24.76.

TABLE 3

Separation of Intermetallic Impurities

| Particle type | Si wt. % | Al wt. % | Fe wt. % | Ca wt. % | Mn wt. % |
|---|---|---|---|---|---|
| $Si_8Al_6Fe_4Ca$. as reported by Margaria et al. | 43.3 | 29.8 | 20.9 | 5.6 | 0.4 |
| Magnetic fraction particle number 1-5 | 40.1 | 24.3 | 18.9 | 4.0 | 0.6 |
| Magnetic fraction particle number 2-5 | 41.4 | 26.4 | 16.5 | 5.8 | 0.6 |
| Magnetic fraction particle number 1BS-4 | 42.9 | 26.1 | 17.0 | 4.5 | 0.7 |

TABLE 4

Poor Separation of Unreacted Comminuted Silicon

| | Weight fraction % | Al wt. % | Ca wt. % | Fe wt. % | Ni wt. % |
|---|---|---|---|---|---|
| Magnetic fraction | 4.3 | 0.17 | 0.12 | 0.32 | 0.006 |

TABLE 4-continued

Poor Separation of Unreacted Comminuted Silicon

| | Weight fraction % | Al wt. % | Ca wt. % | Fe wt. % | Ni wt. % |
|---|---|---|---|---|---|
| Non-magnetic fraction | 95.7 | 0.15 | 0.13 | 0.31 | 0.005 |
| Content Ratio | | 1.13 | 0.92 | 1.03 | 1.20 |

TABLE 5

Superior Separation of Partially Reacted Silicon

| | Weight fraction % | Al wt. % | Ca wt. % | Fe wt. % | Ni wt. % |
|---|---|---|---|---|---|
| Magnetic fraction | 13.3 | 1.02 | 0.58 | 5.6 | 0.05 |
| Non-magnetic fraction | 86.7 | 0.39 | 0.32 | 0.9 | 0.012 |
| Content ratio | | 2.62 | 1.81 | 6.22 | 4.17 |

TABLE 6

Damaging Effect of Iron on Direct Process Selectivity

| | Feed Fe % wt. | T/D ratio |
|---|---|---|
| Standard Metallurgical Grade Silicon | 0.34 | 0.072 |
| Standard Silicon Plus Iron Powder | 0.64 | 0.103 |

TABLE 7

Comparison of Separation Methods

| Separation Method | Fe in feed % wt. | Fe in fraction 1 % wt. | Fe in fraction 2 % wt. | Content Ratio |
|---|---|---|---|---|
| Shah Example 2H | 3.6 | 4.6 | 2.8 | 1.64 |
| Shah Example 4 | 2.5 | 4.9 | 1.9 | 2.58 |
| High Grad. Magnetic Separator Ex. 4 | 1.53 | 5.6 | 0.9 | 6.22 |
| Induced roll Magnet Example 1 | 1.04 | 6.11 | 0.417 | 14.65 |
| Dry Vibrating Magnetic Filter Ex. 2 | 1.0 | 15.0 | 0.58 | 25.86 |

What is claimed is:

1. A process of treating silicon-containing solid material used in a reactor for producing chlorosilanes, the process comprising subjecting the silicon-containing solid material that has been used in said reactor, to a magnetic separator apparatus to separate constituents in the silicon-containing solid material into a magnetic portion and a non-magnetic portion.

2. The process as claimed in claim 1 wherein the magnetic portion is removed from the process.

3. The process of claim 1 wherein the process is carried out at about ambient temperature and pressure.

4. The process of claim 1 wherein the process is carried out above ambient temperature and pressure.

5. The process of claim 4 wherein the process is carried out below 360° C. and below 150 psig.

6. The process of claim 4 wherein the process is carried out in the temperature range of about 150° C. to about 340° C.

7. The process of claim 4 wherein the process is carried out in a pressure range of about 25 to about 45 psig.

8. The process as claimed in claim 1 wherein the process is for the production of alkylchlorosilanes.

9. The process as claimed in claim 1 wherein the process is for the production of trichlorosilane.

10. The process as claimed in claim 1 wherein the process is used in a fluid bed reactor used for producing chlorosilanes by the Direct Process.

11. The process as claimed in claim 1 wherein the silicon-containing solid material is cooled prior to carrying out the magnetic separation.

12. The process as claimed in claim 1 wherein the non-magnetic fraction is heated after being subjected to the magnetic separation.

13. A process as claimed in claim 1 wherein the silicon containing materials that have been used in the reactor are comminuted prior to subjecting the silicon containing materials to the magnetic separator.

14. A process as claimed in claim 1 wherein the silicon containing materials that have been used in the reactor are subject to a size classification process before subjecting the silicon containing materials that have been used in the reactor to a magnetic separator.

15. A process of treating silicon-containing solid material, the process comprising:

(I) removing silicon-containing solid material from a fluid bed of a fluid bed reactor;

(II) subjecting the silicon-containing solid material to a magnetic separator apparatus to separate constituents in the silicon-containing solid material into a magnetic portion and a non-magnetic portion;

(III) returning the non-magnetic portion of the silicon-containing solid material to a fluid bed of a fluid bed reactor.

16. A process for the manufacture of chlorosilanes, said process comprising in a process for the manufacture of chlorosilanes:

(I) treating silicon-containing solid materials by that have been used in a reactor that is used for the manufacture of chlorosilanes by subjecting the silicon-containing solid materials to a magnetic separator apparatus to separate constituents in the silicon-containing solid material into a magnetic portion and a non-magnetic portion;

(II) removing the magnetic portion of the silicon-containing solid materials from the reactor.

17. A process as claimed in claim 16 wherein the silicon-containing solid materials are removed from the reactor before being subjected to magnetic separation.

18. A process as claimed in claim 16 that is the Direct Process for the manufacture of chlorosilanes.

19. A process as claimed in claim 1 wherein the process is a continuous process.

20. A process as claimed in claim 1 wherein the process is a batch process.

21. A silicon-containing material that has been treated by the process of claim 1.

22. A silicon-containing material from a reaction to manufacture chlorosilanes after it has been subjected to Step I as claimed in claimed 16.

23. A process for the preparation of chlorosilanes, the process comprising:

(I) providing a fluid bed reactor;
(II) charging the fluid bed reactor with
  (i) comminuted silicon;
  (ii) at least one catalyst for a Direct Process reaction;
  (iii) at least one promoter for the Direct Process reaction;
(III) thereafter, providing an alkyl chloride to the fluid bed reactor to form a fluid bed in the reactor;
(IV) allowing the comminuted silicon, catalyst, promoter and alkyl chloride to interact and react to produce alkylchlorosilanes at a desired ratio and at a desired rate;
(V) thereafter, upon a certain increase in the desired ratio or a certain reduction in the desired reaction rate, subject the contents of the fluid bed to a process comprising treating the fluid bed contents by subjecting the fluid bed contents to a magnetic separator apparatus to separate constituents in the fluid bed contents into a magnetic portion and a non-magnetic portion and removing the magnetic portion of the fluid bed contents from the process.

24. A process as claimed in claim 23 wherein the contents of the fluid bed are removed from the reactor before they are subjected to magnetic separation.

25. A process for the preparation of chlorosilanes, the process comprising:

(I) providing a fluid bed reactor;
(II) charging the fluid bed reactor with
  (i) comminuted silicon;
  (ii) at least one catalyst for a Direct Process reaction;
  (iii) at least one promoter for the Direct Process reaction;
(III) thereafter, providing an alkyl chloride to the fluid bed reactor to form a fluid bed in the reactor;
(IV) allowing the comminuted silicon, catalyst, promoter and alkyl chloride to interact and react to produce alkylchlorosilanes at a desired ratio and at a desired rate;
(V) thereafter, upon a certain increase in the desired ratio or a certain reduction in the desired reaction rate, subject the contents of the fluid bed to a process comprising treating the fluid bed contents by comminuting the fluid bed contents to reduce the average particle size of the solids therein and thereafter, subjecting the milled fluid bed contents to a magnetic separator apparatus to separate constituents in the fluid bed contents into a magnetic portion and a non-magnetic portion and thereafter, removing the magnetic portion of the fluid bed contents from the process and continuing the Direct Process.

26. A process as claimed in claim 25 wherein the contents of the fluid bed reactor are removed from the reactor before they are subjected to comminuting and magnetic separation.

27. A process for the preparation of chlorosilanes, the process comprising:

(I) providing a fluid bed reactor;
(II) charging the fluid bed reactor with
  (i) comminuted silicon;
  (ii) at least one catalyst for a Direct Process reaction;
  (iii) at least one promoter for the Direct Process reaction;
(III) thereafter, providing an alkyl chloride to the fluid bed reactor to form a fluid bed in the reactor;
(IV) allowing the comminuted silicon, catalyst, promoter and alkyl chloride to interact and react to produce alkylchlorosilanes at a desired ratio and at a desired rate;
(V) thereafter, upon a certain increase in the desired ratio or a reduction in the desired reaction rate, subject the contents of the fluid bed to a process comprising treating the fluid bed contents by reducing and removing impurities from the solids portion of the fluid bed contents by subjecting the fluid bed contents to a size classification method using an aerodynamic centrifugal classifier process and thereafter subjecting the purified fluid bed contents to a magnetic separator apparatus to separate constituents in the fluid bed contents into a magnetic portion and a non-magnetic portion and removing the magnetic portion of the fluid bed contents from the fluid bed reactor and continuing the Direct Process.

28. A process as claimed in claim 27 wherein the fluid bed contents are removed from the reactor before they are subjected to aerodynamic centrifugal classification and magnetic separation.

29. A process for the preparation of chlorosilanes, the process comprising:

(I) providing a fluid bed reactor;

(II) charging the fluid bed reactor with
(i) comminuted silicon;
(ii) at least one catalyst for a Direct Process reaction;
(iii) at least one promoter for the Direct Process reaction;

(III) thereafter, providing an alkyl chloride to the fluid bed reactor to form a fluid bed in the reactor;

(IV) allowing the comminuted silicon, catalyst, promoter and alkyl chloride to interact and react to produce alkylchlorosilanes at a desired ratio and at a desired rate;

(V) thereafter, upon a certain increase in the desired ratio or a reduction in the desired reaction rate, subject the contents of the fluid bed to a process comprising treating the fluid bed contents by comminuting the fluid bed contents to reduce the average particle size of the solids therein and reducing and removing impurities from the milled solids portion of the fluid bed contents by subjecting the fluid bed contents to a size classification method using an aerodynamic centrifugal classifier process and then subjecting the purified fluid bed contents to a magnetic separator apparatus to separate constituents in the fluid bed contents into a magnetic portion and a non-magnetic portion and then removing the magnetic portion of the fluid bed contents from the fluid bed of the fluid bed reactor and continuing the Direct Process.

30. The process as claimed in claim 29 wherein the fluid bed contents are removed from the reactor before comminuting, aerodynamic centrifugal classification and magnetic separation.

31. A process for the preparation of chlorosilanes, the process comprising:

(I) providing a fluid bed reactor;

(II) charging the fluid bed reactor with
(i) comminuted silicon;
(ii) at least one catalyst for a Direct Process reaction;
(iii) at least one promoter for the Direct Process reaction;

(III) thereafter, providing an alkyl chloride to the fluid bed reactor to form a fluid bed in the reactor;

(IV) allowing the comminuted silicon, catalyst, promoter and alkyl chloride to interact and react to produce alkylchlorosilanes at a desired ratio and at a desired rate;

(V) thereafter, upon a certain increase in the desired ratio or a certain reduction in the desired reaction rate, subject the contents of the fluid bed to a process comprising treating the fluid bed contents by abrading the fluid bed contents to remove impurities from the surface of the fluid bed contents particle and thereafter, subjecting the abraded fluid bed contents to a magnetic separator apparatus to separate constituents in the fluid bed contents into a magnetic portion and a non-magnetic portion and thereafter, removing the magnetic portion of the fluid bed contents from the process and continuing the Direct Process.

32. A process as claimed in claim 31 wherein the fluid bed contents are removed from the reactor to undergo the abrasion before they are subjected to magnetic separation.

* * * * *